United States Patent [19]

Pilgram

[11] 4,257,805

[45] Mar. 24, 1981

[54] HERBICIDAL (4-SUBSTITUTED-PHENYLAMINO)-3-(TRI-FLUOROMETHYL)PHENYL)UREAS

[75] Inventor: Kurt H. Pilgram, Modesto, Calif.

[73] Assignee: Shell Oil Company, Houston, Tex.

[21] Appl. No.: 110,972

[22] Filed: Jan. 10, 1980

Related U.S. Application Data

[63] Continuation of Ser. No. 19,376, Mar. 12, 1979, abandoned.

[51] Int. Cl.$^3$ ..................... A01N 47/30; C07C 127/15
[52] U.S. Cl. .......................................... 71/120; 564/50

[58] Field of Search ...................... 71/120; 260/553 A

[56] References Cited

U.S. PATENT DOCUMENTS

| | | | |
|---|---|---|---|
| 3,396,005 | 8/1968 | Popoff | 71/120 X |
| 3,419,664 | 12/1968 | Frick | 424/322 |
| 3,660,486 | 5/1972 | Thiele | 260/553 A |

Primary Examiner—Catherine L. Mills

[57] ABSTRACT

Certain (4-(substituted-phenylamino)-3-(trifluoromethyl)phenyl)ureas, and their use as herbicides.

3 Claims, No Drawings

HERBICIDAL (4-SUBSTITUTED-PHENYLAMINO)-3-(TRI-FLUOROMETHYL)PHENYL)UREAS

This is a continuation of application Ser. No. 19,376, filed Mar. 12, 1979, now abandoned.

DESCRIPTION OF THE INVENTION

It has been found that useful herbicidal properties are possessed by ureas of the formula:

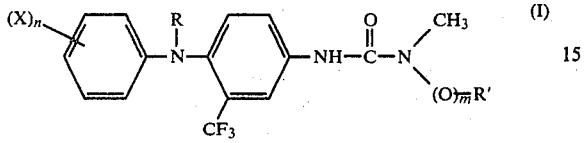

wherein R and R' each is hydrogen or alkyl of from one to three carbon atoms; m is zero or one; with the proviso that when m is 1, R' is not hydrogen; X is halogen, trifluoromethyl, or alkyl or alkoxy of from one to three carbon atoms, and n is one or two, with the proviso that no more than one of X is trifluoromethyl.

The alkyl moieties represented by R, R' and X may be straight-chain or branched-chain in configuration. By the term "halogen" is meant chlorine, bromine and fluorine.

Typical, exemplary individual species of this class of compounds, the manner in which they can be prepared and isolated, and summaries of the results of their herbicidal testing, are set forth in the Examples hereinafter. Other, typical individual species of the class are the following (in which the symbols refer to Formula I)

| $(X)_n$ | R | R' | m |
|---|---|---|---|
| 2-chloro, 5-trifluoromethyl | H | methyl | zero |
| 2-chloro, 4-trifluoromethyl | H | methyl | zero |
| 4-bromo, 2-trifluoromethyl | H | methyl | zero |
| 4-chloro, 2-trifluoromethyl | H | methyl | zero |

Compounds of Formula I can be prepared by three general methods, in which the first three steps are as follows:

1. The $(X)_n$-substituted aniline is treated with formic acid to form the corresponding N-formanilide. The treatment is conveniently carried out by refluxing the aniline/formic acid mixture. Those species wherein R is alkyl can be prepared by treating the sodium salt of the formanilide (see step 2, next) with the appropriate R-halide, preferably iodide or bromide, suitably in a solvent such as tetrahydrofuran.

2. the formanilide is treated with a one-molar equivalent of sodium hydride in dimethylformamide and the resulting solution of the sodium salt is treated with 2-chloro-5-nitrobenzotrifluoride (U.S. Pat. No. 3,657,350) at an elevated temperature (e.g., 155° C., reflux), to give the 4-nitrodiphenylamine (J. Organic Chemistry, 42, 1786 (1977) and references therein).

3. The 4-nitrodiphenylamine is conveniently reduced to the 4-aminodiphenylamine by treatment with hydrogen in a Parr shaker at room temperature employing Raney nickel or palladium-on-charcoal as catalyst, and a solvent such as tetrahydrofuran.

4. The 4-aminodiphenylamine is converted to the desired urea product by one of three procedures:

4a. It is treated with methyl isocyanate to give the desired urea wherein m is zero and R' is hydrogen. The treatment is conveniently conducted by heating a mixture of the reactants, in a solvent such as tetrahydrofuran at an elevated temperature, as on a steam bath.

4b. It is treated with the appropriate N-methyl-N-R'-carbamoyl chloride or N-methyl-N-(R'-oxy)carbamoyl chloride in the presence of a molar equivalent of a tertiary amine (triethylamine, pyridine, ethyldiisopropylamine, collidine), to give the desired urea wherein m is zero and R' is alkyl or wherein m is 1 and R' is alkyl, respectively. The treatment is carried out at a moderately elevated temperature, for example at reflux.

4c. The 4-aminodiphenylamine is treated with phosgene to form the corresponding isocyanate, which is treated with the methyl-R'-amine. The reaction of the amine with phosgene is conveniently conducted by slowly introducing a solution of the amine in a solvent such as ethyl acetate into a solution of a stoichiometric excess of phosgene in the same solvent, at room temperature, refluxing the mixture and then heating it to a higher temperature (of the order of 75°–80° C.) by gradually allowing some of the excess phosgene to distil from the mixture. The isocyanate is converted to the urea by treating it with an excess of the amine in a solvent such as ether, conveniently at room temperature.

Some of the precursors are known compounds; the others can be prepared by known methods, as illustrated in the Examples, hereinafter.

The preparation and isolation of typical individual species of compounds of Formula I are shown in the following examples. In each case, the identities of the product, and of each intermediate involved, was confirmed by appropriate chemical and spectral analyses.

EXAMPLE

1—N'-(4-(3-chloro-4-fluorophenylamino)-3-(trifluoromethyl)phenyl)-N,N-dimethylurea (1)

A mixture of 100 g of 3-chloro-4-fluoroaniline and 400 ml of 97% formic acid was refluxed (106° C.) for three hours. The mixture then was poured into ice water and the resulting mixture was filtered. The solid was washed with water and dried to give N-(3-chloro-4-fluorophenyl)formamide (J. Org. Chem., 26, 2563 (1961)) (1A), as a colorless crystalline solid, mp: 94°–97° C.

15.8 g of sodium hydride (57% in mineral oil) was added in portions to a stirred solution of 52 g of 1A in 300 ml of dimethylformamide, the temperature of the mixture rising to 60° C. The mixture was heated to and held at 95° C. for 10 minutes. It then was cooled and treated with 67.6 g of 2-chloro-5-nitrobenzotrifluoride. The mixture was refluxed (163° C.) for four hours, then was cooled and poured into ice water. The resulting mixture was extracted with ether. The ether extracts were dried and the ether was evaporated. The residue was purified by silica gel chromatography to give 3'-chloro-4'-fluoro-4-nitro-2-(trifluoromethyl)diphenylamine, as a light-yellow solid (1B) mp: 85°–87° C.

A solution of 85 g of 1B in 250 ml of tetrahydrofuran was hydrogenated over Raney nickel at room temperature and 60 psig hydrogen pressure to give 4-amino-3'-chlor0-4'-fluoro-2-(trifluoromethyl)diphenylamine (1C) as an amber syrup.

A solution of 20 g of 1C in 150 ml of ethyl acetate was added drop-by-drop over a 30-minute period to a stirred solution of 20 g of phosgene in 100 ml of ethyl acetate. The resulting mixture was heated at 50° C. for three hours, then for two hours at 78° C. while phosgene was allowed to distil from the mixture. The solvent was evaporated under reduced pressure to give 4-(3-chloro-4-fluorophenylamino)-3-(trifluoromethyl)phenyl isocyanate (1D), as an amber syrup.

An excess of anhydrous dimethylamine was introduced into a solution of 22 g of 1D in 250 ml of anhydrous ether. The resulting mixture was held for 18 hours at room temperature, then the ether was evaporated under reduced pressure. The residue was purified by silica gel chromatography to give 1, as an amber syrup.

EXAMPLE
2—N,N-dimethyl-N'-(4-(4-isopropoxy-3-(trifluoromethyl)phenylamino)-3-(trifluoromethyl)phenyl)urea (2)

A solution of 41 g of sodium isopropoxide in 300 ml of dimethyl sulfoxide was added drop-by-drop to a chilled (5° C.) solution of 118 g of 2-chloro-5-nitrobenzotrifluoride in 100 ml of dimethyl sulfoxide. The resulting mixture was stirred at room temperature for one hour, poured into water, and the resulting mixture was extracted with ether. The extract was washed with water, dried, and the solvent was evaporated. The liquid residue was taken up in hexane and the solution was chilled to give a solid, which on recrystallization from hexane gave 2-isopropoxy-5-nitrobenzotrifluoride (2A), as a white crystalline solid, mp: 34°–36° C.

137.5 g of iron filings were added in portions to a refluxing mixture of 113.3 g of 2A, 1200 ml of 5% aqueous acetic acid and 50 ml of methanol. The resulting mixture was refluxed for one hour and filtered while hot. Work-up by either extraction of the cooled filtrate gave 4-isopropoxy-3-(trifluoromethyl)aniline (2B), as an amber oil.

A mixture of 54.8 g of 2B and 200 ml of 98% formic acid was refluxed for one hour, cooled and poured into ice water. The resulting mixture was extracted with ether. The extract was washed, successively, with aqueous soidum bicarbonate and water, dried and the solvent was evaporated under reduced pressure. The residue, a syrup, crystallized from 1/5 v/v ether/hexane to give N-(4-isopropoxy-3-(trifluoromethyl)phenyl)formamide (2C), as a tan solid, mp: 80°–82° C.

10.4 g of sodium hydride (57% in mineral oil) was added to a stirred solution of 48-7 g of 2C in 200 ml of dimethylformamide at room temperature. The temperature of the mixture rose to 55° C. The resulting mixture was held at room temperature for one hour. Then 49.4 g of 2-chloro-5-nitrobenzotrifluoride was added. Gas evolution occurred, and when it ceased, the resulting mixture was poured into ice water and extracted with ether. The ether was evaporated and the residue was purified by silica gel chromatography to give 4-isopropoxy-2',3-bis-(trifluoromethyl)-4'-nitrodiphenylamine (2D), as a yellow solid, mp: 98°–100° C.

A mixture of 42.2 g of 2D and 2 g of Raney nickel in 200 ml of tetrahydrofuran was hydrogenated at room temperature under 60 psig of hydrogen. After two hours, the resulting mixture was filtered and the solvent was evaporated under reduced pressure to give 4'-amino-2',3-bis(trifluoromethyl)-4-isopropoxydiphenylamine (2E), as an amber syrup.

A solution of 9 g of 2E in 50 ml of ethyl acetate was added drop-by-drop to a stirred solution of 20 g of phosgene in 150 ml of ethyl acetate at room temperature. The resulting mixture was heated to and held at 55° C. for two hours, then at 78° C. for one hour, excess phosgene being allowed to distil from the mixture. The solvent was evaporated from the resulting mixture under reduced pressure to give 4-(4-isopropoxy-3-(trifluoromethyl)phenylamino)-3-(trifluoromethyl)phenyl isocyanate (2F), as an amber oil.

A solution of 9.6 g of 2F in ether was treated with an excess of anhydrous dimethylamine, giving 2, as an off-white solid, mp: 102°–105° C.

EXAMPLE
3—N'-(4-(3,4-dichlorophenylamino)-3-(trifluoromethyl)phenyl)-N-methoxy-N-methylurea (3)

A mixture of 81 g of 3,4-dichloroaniline and 405 ml of 90% formic acid was stirred and refluxed (106° C.) for two hours. The mixture then was poured over ice water. The mixture was filtered and the solid was washed with water and dried to give 3,4-dichloroformanilide (J. Org. Chem., 23, 727 (1958)) (3A), as an off-white solid, mp: 108°–111° C.

21.5 g of sodium hydride (57% in mineral oil) was added in portions to a stirred solution of 91.7 g of 3A in 300 ml of dimethylformamide. The resulting mixture was heated to and held at 100° C. for five minutes, then cooled to 30° C. and 108.8 g of 2-chloro-5-nitrobenzotrifluoride was added. The resulting stirred mixture was heated to and held at 160° C. for four hours. The resulting mixture was poured over ice and extracted with ether. The extract was dried and the ether was evaporated to give an amber syrup, which was chromatographed over silica gel to give 3,4-dichloro-4'-nitro-2'-(trifluoromethyl)diphenylamine (3B), as a yellow solid, mp: 77°–79° C.

A solution of 84 g of 3B in 300 ml of tetrahydrofuran was hydrogenated over Raney nickel at room temperature and 60 psig hydrogen pressure for 18 hours. The resulting mixture was filtered and the solvent was evaporated. Crystallization of the residual oil from 1/6 v/v ether/hexane gave 4'-amino-3,4-dichloro-2'-(trifluoromethyl)diphenylamine (3C), as a colorless solid, mp: 89°–91° C.

A solution of 13.3 g of 3C, 4.2 g of triethylamine and 5.2 g of N-methoxy-N-methylcarbamoyl chloride in 100 ml of tetrahydrofuran was stirred and refluxed for 18 hours. The resulting mixture was poured into ice water, and extracted with ether. The ether extract was dried and the solvent was evaporated. The residue crystallized from 1/6 v/v ether/hexane to give 3, as a colorless solid, mp: 117°–119° C.

EXAMPLE
4—N-(4-(4-bromo-3-chlorophenylamino)-3-trifluoromethyl)phenyl)-N'-methylurea (4)

A mixture of 60.7 g of 4-bromo-3-chloroaniline and 300 ml of 97% formic acid was refluxed for four hours. The resulting mixture was poured over ice and filtered. The solid was washed with water and recrystallized from 3/1 v/v ether/hexane to give N-(4-bromo-3-chlorophenyl)formamide (4A), as a tan solid, mp: 110°–113° C.

16.1 g of sodium hydride (57% in oil) was added in portions to a stirred solution of 64 g of 4A in 300 ml of dimethylformamide. The temperature of the mixture rose to 60° C. The resulting mixture was cooled to 30°

C. while 61.6 g of 2-chloro-5-nitrobenzotrifluroide was added. The resulting mixture was heated to and held at 160° C. for three hours, cooled and diluted with ice water. The resulting mixture was acidified (HCl) and extracted with ether. The extract was washed with water, dried and the solvent was evaporated to given an amber syrup. Purification of the syrup by silica gel chromatography gave 4-bromo-3-chloro-2'-(trifluoromethyl)-4-nitrodiphenylamine (4B), as a yellow solid, mp: 106°–108° C.

A solution of 50 g of 4B in 150 ml of tetrahydrofuran was hydrogenated for four hours over Raney nickel at room temperature and 60 psig hydrogen pressure. The resulting mixture was filtered and the solvent was evaporated from the filtrate to give a viscous oil. Crystallization from hexane gave 4'-amino-4-bromo-3-chloro-2'-(trifluoromethyl)diphenylamine (4C), as a colorless solid, mp: 95°–97° C.

A sealed glass cylinder containing 1 g of 4C, 1 g of methyl isocyanate and 10 ml of tetrahydrofuran was placed on a steam bath for 18 hours. The solvent was evaporated from the resulting mixture and the residue was purified by silica gel chromatography to give 4, as a colorless solid, mp: 136°–139° C. and 149°–151° C.

EXAMPLE 5—N,N-dimethyl-N'-(4-((3-chloro-4-fluorophenyl)methylamino)-3-(trifluoromethyl)phenyl)urea (5)

17.5 g of sodium hydride (57% in mineral oil) was added, in portions, to a stirred solution of 55.5 g of 1A and 71 g of methyl iodide in 250 ml of tetrahydrofuran at room temperature. The resulting mixture was stirred and refluxed for 2 hours, poured into ice water and filtered. The solid was washed with water, dried and recrystallized from hexane to give N-(3-chloro-4-fluorophenyl)N-methylformamide (5A), as a white crystalline solid, mp: 47°–48° C.

A mixture of 42.2 g of 5A and 50 g of concentrated sulfuric acid in 600 ml of water was refluxed for 7 hours. The resulting mixture was charcoaled, filtered, cooled to 10° C. and made alkaline with sodium hydroxide. The resulting mixture was extracted with ether. The extract was dried and the ether evaporated to give 3-chloro-4-fluoro-N-methyl-aniline, (5B), as a yellow oil.

10.2 g of sodium hydride (57% in mineral oil) was added, in portions, to a stirred solution of 31 g of 5B and 43.7 g of 2-chloro-5-nitrobenzotrifluoride in 300 ml of dimethylformamide at room temperature. The resulting mixture was refluxed for two hours and poured into ice water, and extracted with ether. The extract was purified by silica gel chromatography to give 3-chloro-4-fluoro-N-methyl-2'-(trifluoromethyl)-4'-nitrodiphenylamine (5C), as a red-orange oil.

A solution of 53.5 g of 5C in 300 ml of tetrahydrofuran was hydrogenated at room temperature and 60 psig hydrogen pressure for 5 hours. The resulting mixture was filtered and the solvent was evaporated from the filtrate to give 4'-amino-2'-(trifluoromethyl)-3-chloro-4-fluoro-N-methyldiphenylamine (5D), as a yellow oil.

A solution of 16.4 g of 5D in 75 ml of tetrahydrofuran was added to a stirred solution of 20 g of phosgene in 150 ml of ethyl acetate at room temperature. The resulting mixture was refluxed (98° C.) for four hours, then the solvent and excess phosgene were distilled off to give 4-((3-chloro-4-fluorophenyl)methylamino)-3-(trifluoromethyl)-phenyl isocyanate (5E), as an amber syrup.

As excess of dimethylamine was added to a solution of 17 g of 5E in 150 ml of anhydrous ether at room temperature. The resulting mixture was washed with dilute hydrochloric acid and then with water, dried, and after filtration concentrated to 50 ml volume. 50 ml of hexane was added and the resulting solution was cooled to 5° C. Filtration gave 4, as a cream-colored solid, mp: 144°–146° C.

By the procedures described in Examples 1–5, the following further individual species of the compounds of Formula I were prepared, the compounds being defined in terms of Formula I:

EXAMPLES 6–12

Subgenus wherein R and R' each is hydrogen and m is zero:

| Example No. | Compound No. | $(X)_n$ | Melting Point (°C.) |
|---|---|---|---|
| 6 | 6 | 3-Cl,4-F | 131–134 |
| 7 | 7 | 3,4-Cl$_2$ | 149–152 |
| 8 | 8 | 3,5-(—OCH$_3$)$_2$ | 113–115 |
| 9 | 9 | 3,5-(—CH$_3$)$_2$ | 157–159 |
| 10 | 10 | 2-Cl | 117–120 |
| 11 | 11 | 2,6-Cl$_2$ | 184–186 |
| 12 | 12 | 2,4-F$_2$ | 74–76 |

EXAMPLES 13–24

Subgenus wherein R is hydrogen, m is zero and R' is methyl:

| Example No. | Compound No. | $(X)_n$ | Melting Point (°C.) |
|---|---|---|---|
| 13 | 13 | 3-(CF$_3$),4-F | 132–133 |
| 14 | 14 | 4-Cl | oil |
| 15 | 15 | 3,4-Cl$_2$ | 135–138 |
| 16 | 16 | 3-(—CF$_3$),4-Cl | 116–119 |
| 17 | 17 | 3-Cl,4-Br | 136–138 |
| 18 | 18 | 3,5-(—CH$_3$)$_2$ | 135–138 |
| 19 | 19 | 2-Cl | 115–118 |
| 20 | 20 | 2,6-Cl$_2$ | 178–180 |
| 21 | 21 | 2,5-Cl$_2$ | 147–148 |
| 22 | 22 | 3,5-Cl$_2$ | 147–150 |
| 23 | 23 | 2,4-F$_2$ | 122–124 |
| 24 | 24 | 3,5-(—OCH$_3$)$_2$ | oil |

EXAMPLES 25–26

Subgenus wherein R is hydrogen, m is one and R' is methyl:

| Example No. | Compound No. | $(X)_n$ | Melting Point (°C.) |
|---|---|---|---|
| 25 | 25 | 3-Cl,4-F | oil |
| 26 | 26 | 3-Cl,4-Br | 124–126 |

EXAMPLES 27–28

Subgenus wherein R is methyl and $(X)_n$ is 3-Cl,4-F:

| Example No. | Compound No. | m | R' | Melting Point (°C.) |
|---|---|---|---|---|
| 27 | 27 | 0 | H | oil |
| 28 | 28 | 1 | methyl | oil |

Compounds of Formula I have been found to be useful for killing unwanted plants, being active with respect to both broadleaved plants and grasses, and being primarily effective when applied postemergence—i.e., applied to the foliage of the plants.

Accordingly, the invention includes a method of killing unwanted plant growth which comprises applying to the plants an effective amount of a compound of Formula I. Likewise, the invention also includes plant growth inhibiting compositions comprising a carrier or a surface-active agent, or both a carrier and a surface-active agent, and, as active ingredient at least one compound of Formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids of aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide an/or propylene oxide; condensation products of fatty alcohols or alkyl phenols, for example p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl solfonates such as sodium dodecylbenzene sulfonate; and polymers of ethylene oxide and copolymers of ethylene oxide and propylene oxides.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing $\frac{1}{2}$–10% by weight of toxicant. Granules are usually prepared to have a size between 10 and 100 BS mesh (1.676–0.152 mm), and may be manufactured by agglomeration or impregnation techniques. Generally, granules will contain $\frac{1}{2}$–25% by weight toxicant and 0–1% by weight of additives such as stabilizers, slow release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight toxicant, 0.5–5% weight of dispersing agents 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds pssessing pesticidal, especially insecticidal, acaricidal, herbicidal or fungicidal properties.

The method of applying the compounds of this invention comprises applying a compound of Formula I, ordinarily in a composition of one of the aforementioned types, to a locus or area to be protected from undesirable plant growth such as the foliage of the plants or the plant growth medium, e.g., soil in which the plant is growing or is to be grown. The active compound, of course, is applied in an amount sufficient to exert the desired action.

The amount of compound of the invention to be used in controlling undesirable vegetation will naturally depend on the condition of the vegetation, the degree of activity desired, the formulation used, the mode of application, the climate, the season of the year, and other variables. Recommendations as to precise amounts are, therefore, not possible. In general, however, application to the locus to be protected of from 0.1 to 10.0 kilograms per hectare of the compound used in this invention will be satisfactory.

EXAMPLES OF HERBICIDAL ACTIVITY

In the following examples the species of weeds that were tested were: barnyard grass — *Echinochloa crusgalli;* crabgrass — *Digitaria sanguinalis;* downy brome — *Bromus tectorum;* yellow foxtail — *Setaria lutescens;* redroot Pigweed — *Amaranthus retroflexus;* sicklepod — *Cassia obtusifolia;* velvetleaf — *Abutilon theophrasti;* and garden cress — *Lepidium sativum.*

The preemergence herbicidal activity of the compounds of the invention was evaluated by planting seeds of barnyard grass, garden cress, downy brome, velvetleaf, yellow foxtail, and sicklepod in test tubes, nominally measuring 25 × 200 millimeters, filled about three-quarters full of untreated soil, in each case covered on top with about 2.5 cubic centimeters of soil treated with the test compound at the rates of 0.1 and 1 milligram, respectively, Table I, Rates I and II, respectively. The dosages of test compound were approximately two and twenty pounds per acre, respectively.

The planted soil was held under controlled conditions of temperature, moisture, and light for 9 to 10 days. The amount of germination and growth in each tube were evaluated on a 0 to 9 scale, 0 rating indicating no effect, 9 death of the seedlings or no germination.

The postemergence activity of the compounds of this invention was evaluated by spraying 10-day old crabgrass plants, 13-day old pig-weed plants, 6-day old downy brome plants, 9-day old velvetleaf, 9-day old yellow foxtail plants and 9-day old sicklepod plants to runoff with a liquid formulation of the test compound at the rates of 2.4 milliliters of an 0.025% solution designated Rate I in Table I, and 2.4 milliliters of an 0.25% solution designted Rate II in Table I. The sprayed plants were held under controlled conditions for 7 to 8 days and the effect of the test compound was then evaluated visually, the results being rated on a 0 to 9 scale, a 0 rating indicating no effect, a 9 rating indicating complete death of the plants.

The results of the tests are summarized in Table I.

TABLE I

HERBICIDE SCREEN RESULTS

| Compound | Preemergence (Soil) Barnyard grass | Garden Cress | Downy Brome | Velvetleaf | Yellow Foxtail | Sicklepod | Postemergence (Foliar) Crabgrass | Pigweed | Downy Brome | Velvetleaf | Yellow Foxtail | Sicklepod |
|---|---|---|---|---|---|---|---|---|---|---|---|---|
| 1 (I) | 3 | 7 | 3 | 3 | 2 | 4 | 8 | 9 | 6 | 9 | 6 | 8 |
| 1 (II) | 5 | 9 | 5 | 6 | 3 | 9 | 8 | 9 | 8 | 9 | 9 | 9 |
| 2 (I) | 2 | 3 | 0 | 0 | 0 | 0 | 7 | 9 | 3 | 6 | 6 | 6 |
| 2 (II) | 2 | 5 | 0 | 2 | 3 | 2 | 9 | 9 | 8 | 8 | 7 | 9 |
| 3 (I) | 0 | 2 | 0 | 2 | 0 | 0 | 9 | 9 | — | 7 | 7 | 6 |
| 3 (II) | 0 | 3 | 0 | 3 | 0 | 2 | 9 | 9 | — | 9 | 8 | 9 |
| 4 (I) | 0 | 0 | 0 | 0 | 0 | 0 | 9 | 9 | 6 | 7 | 7 | 7 |
| 4 (II) | 0 | 0 | 0 | 0 | 0 | 0 | 9 | 9 | 9 | 9 | 9 | 9 |
| 5 (I) | 2 | 4 | 2 | 2 | 0 | 0 | 8 | 9 | 7 | 9 | 8 | 8 |
| 5 (II) | 7 | 8 | 4 | 6 | 0 | 0 | 8 | 9 | 9 | 9 | 9 | 9 |
| 6 (I) | 0 | 4 | 0 | 3 | — | 4 | 8 | 8 | 5 | 8 | 8 | 8 |
| 6 (II) | 0 | 9 | 0 | 7 | — | 7 | 9 | 9 | 5 | 9 | — | 9 |
| 7 (I) | 0 | 0 | 0 | 0 | 3 | 7 | 8 | 9 | 9 | 8 | 9 | 7 |
| 7 (II) | 0 | 3 | 6 | 8 | 3 | 7 | 9 | 9 | 9 | 9 | 9 | 9 |
| 8 (I) | 2 | 3 | 0 | 0 | — | 0 | 0 | 0 | 3 | 7 | 0 | 5 |
| 8 (II) | 2 | 3 | 2 | 3 | 6 | 0 | 7 | 9 | 7 | 9 | 8 | 8 |
| 9 (I) | 0 | 0 | 0 | 0 | 0 | 0 | 7 | 7 | 7 | 9 | 9 | 8 |
| 9 (II) | 0 | 0 | 0 | 0 | 0 | 0 | 9 | 9 | 8 | 7 | 7 | 9 |
| 10 (I) | 0 | 0 | 0 | 0 | 0 | 0 | 7 | 6 | 5 | 8 | 5 | 8 |
| 10 (II) | 0 | 0 | 3 | 2 | 0 | 0 | 9 | 9 | 9 | 9 | 9 | 9 |
| 11 (I) | 0 | 0 | 0 | 0 | 0 | 0 | 7 | 5 | 2 | 6 | 5 | 7 |
| 11 (II) | 2 | 3 | 0 | 0 | 0 | 0 | 9 | 9 | 6 | 8 | 8 | 9 |
| 12 (I) | 0 | 3 | 2 | 1 | 0 | 1 | 8 | 9 | 7 | 9 | 9 | 7 |
| 12 (II) | 0 | 9 | 2 | 3 | 0 | 2 | 9 | 9 | 9 | 9 | 9 | 9 |
| 13 (I) | 2 | 7 | 0 | 0 | 0 | 0 | 6 | 9 | 3 | 7 | 9 | 7 |
| 13 (II) | 0 | 9 | 0 | 2 | 3 | 6 | 7 | 9 | 7 | 8 | 9 | 9 |
| 14 (I) | 2 | 6 | 2 | 0 | 0 | 0 | 0 | 9 | 3 | 6 | 9 | 9 |
| 14 (II) | 7 | 8 | 6 | 2 | 5 | 3 | 9 | 9 | 6 | 9 | 9 | .9 |
| 15 (I) | 0 | 2 | 0 | 0 | 0 | 0 | 9 | 9 | 5 | 8 | 9 | 7 |
| 15 (II) | 0 | 3 | 0 | 0 | 0 | 0 | 9 | 9 | 9 | 9 | 9 | 9 |
| 16 (I) | 0 | 4 | 2 | 2 | 0 | 0 | 6 | 8 | 4 | 8 | 6 | 6 |
| 16 (II) | 0 | 8 | 3 | 2 | 0 | 2 | 8 | 9 | 4 | 9 | 9 | 9 |
| 17 (I) | 0 | 0 | 0 | 0 | 0 | 0 | 9 | 9 | 3 | 9 | 9 | 9 |
| 17 (II) | 0 | 4 | 4 | 3 | 0 | 0 | 9 | 9 | 9 | 9 | 9 | 9 |
| 18 (I) | 0 | 2 | 0 | 2 | 0 | 0 | 9 | 9 | 8 | 9 | 7 | 9 |
| 18 (II) | 0 | 5 | 0 | 4 | 2 | 2 | 9 | 9 | 9 | 9 | 9 | 9 |
| 19 (I) | 0 | 0 | 0 | 0 | 0 | 0 | 8 | 9 | 8 | 8 | 9 | 9 |
| 19 (II) | 0 | 7 | 4 | 2 | 0 | 0 | 8 | 9 | 8 | 9 | 9 | 9 |
| 20 (I) | 0 | 0 | 0 | 0 | 0 | 0 | 9 | 9 | 3 | 8 | 9 | 9 |
| 20 (II) | 0 | 5 | 0 | 0 | 0 | 0 | 9 | 9 | 7 | 9 | 9 | 9 |
| 21 (I) | 0 | 0 | 0 | 0 | 0 | 0 | 8 | 8 | 6 | 7 | 8 | 7 |
| 21 (II) | 0 | 0 | 3 | 0 | 0 | 0 | 9 | 9 | 9 | 9 | 9 | 8 |
| 22 (I) | 0 | 0 | 0 | 0 | 0 | 0 | 8 | 9 | — | 7 | — | 8 |
| 22 (II) | 2 | 2 | 0 | 0 | 0 | 0 | 9 | 9 | — | 9 | — | 9 |
| 23 (I) | 0 | 7 | 0 | 0 | 0 | 2 | 8 | 9 | 9* | 9 | 9 | 7 |
| 23 (II) | 4 | 8 | 7 | 5 | 0 | 4 | 9 | 9 | 9 | 9 | 9 | 9 |
| 24 | 5 | 5 | 6 | 7 | 7 | 5 | 6 | 7 | 4 | 6 | 7 | 4 |

TABLE I-continued

| | HERBICIDE SCREEN RESULTS | | | | | | | | | | | |
|---|---|---|---|---|---|---|---|---|---|---|---|---|
| | Preemergence (Soil) | | | | | | Postemergence (Foliar) | | | | | |
| | Barn-yard grass | Gar-den Cress | Downy Brome | Vel-vet-leaf | Yel-low Fox-tail | Sickle-pod | Crab-grass | Pig-weed | Downy Brome | Vel-vet-leaf | Yel-low Fox-tail | Sickle-pod |
| | | | | | | Dosage | | | | | | |
| Compound | I  II | I  II | I  II | I  II | I  II | I  II | I  II | I  II | I  II | I  II | I  II | I  II |
| 25 | 7  0 | 8  5 | 8  0 | 8  0 | 7  0 | 7  0 | 8  8 | 9  9 | 8  7 | 7  9 | 6  9 | 9  9 |
| 26 | 5  0 | 9  0 | 3  0 | 8  0 | 7  0 | 7  0 | 9  9 | 9  9 | 5  9 | 8  9 | 7  9 | 9  9 |
| 27 | 0  0 | 5  5 | 0  0 | 0  3 | 0  0 | 0  3 | 9  9 | 9  9 | 9  8 | 9  9 | 9  9 | 9  9 |
| 28 | 0  2 | 2  7 | 0  0 | 0  3 | 0  3 | 0  3 | 7  9 | 9  9 | 4  5 | 8  9 | 7  8 | 7  8 |

*Johnson grass instead of downy brome.

We claim:
1. A compound of the formula:

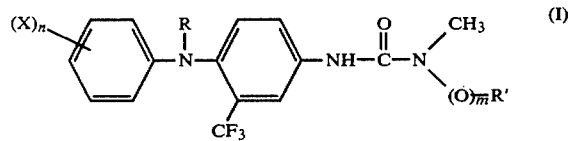

wherein R and R' each is hydrogen or alkyl of from one to three carbon atoms; m is zero or one, with the proviso that when m is 1, R' is not hydrogen; X is halogen, trifluoromethyl, or alkyl or alkoxy of from one to three carbon atoms, and n is one or two, with the proviso that no more than one of X is trifluoromethyl.

2. A herbicidal composition comprising a herbicidal amount of a compound of claim 1 and at least one surface active agent or carrier therefore.

3. A method for killing unwanted plants which comprises applying to the unwanted plants a herbicidal amount of a compound of claim 1 or a composition containing it.

* * * * *